United States Patent [19]

Kurachi et al.

[11] Patent Number: 4,863,583
[45] Date of Patent: Sep. 5, 1989

[54] ELECTRODE STRUCTURE OF AN OXYGEN SENSING ELEMENT

[75] Inventors: Hiroshi Kurachi, Konan; Fujio Ishiguro, Nagoya; Nobuhide Kato, Aichi, all of Japan

[73] Assignee: NGK Insulators, Ltd., Nagoya, Japan

[21] Appl. No.: 183,997

[22] Filed: Apr. 20, 1988

[30] Foreign Application Priority Data

Apr. 24, 1987 [JP] Japan .................. 62-102189

[51] Int. Cl.$^4$ ............................................ G01N 27/58
[52] U.S. Cl. ...................... 204/424; 204/426; 204/429
[58] Field of Search ............... 204/424, 425, 426, 427, 204/428, 429, 1 S

[56] References Cited

U.S. PATENT DOCUMENTS 3,645,875  2/1972  Record et al. ................. 204/429
4,199,425  4/1980  Sinkevitch ..................... 204/429
4,655,892  4/1987  Satta et al. ................. 204/424 X

FOREIGN PATENT DOCUMENTS 60-144659  7/1985  Japan .
61-117950  1/1986  Japan .
61-30760   2/1986  Japan .
123351     6/1987  Japan .................. 204/424

Primary Examiner—G. L. Kaplan
Attorney, Agent, or Firm—Arnold, White & Durkee

[57] ABSTRACT

An electrode formed on an oxygen-ion conductive solid electrolyte body of an oxygen sensing element such that the electrode is exposed to a measurement fluid to be measured, for detecting a concentration of oxygen in the fluid. The electrode is formed of a porous cermet layer which has a thickness of at least 3 microns. The porous cermet layer includes as major components thereof an oxygen-ion conductive solid electrolyte, and at least two platinum-group metals which are selected from the platinum group and which includes platinum and rhodium. A content of said rhodium and a total content of the above at least two platinum-group metals are determined so as to satisfy the following formulas: $R/M = 0.2$ to $0.8$, and $M/(SE+M) = 0.3$ to $0.8$, where, $R$ = volume % of rhodium included in the cermet layer, $M$ = total volume % of the at least two platinum-group metals, and $SE$ = volume % of the oxygen-ion conductive solid electrolyte included in the cermet layer.

10 Claims, 5 Drawing Sheets

ELECTRODE STRUCTURE OF AN OXYGEN SENSING ELEMENT

BACKGROUND OF THE INVENTION

1. Field of the Invention

The present invention relates in general to the structure of an electrode used in an oxygen sensor, and more particularly to the electrode structure formed on an oxygen-ion conductive solid electrolyte body of an oxygen sensing element of such an oxygen sensor such that the electrode structure contacts a fluid to be measured, for detecting the concentration of oxygen in the fluid in an accurate manner, even where the fluid contains unburned components or imcombustibles, in particular, oxides of nitrogen (NOx).

2. Discussion of the Prior Art

There is known an oxygen sensor for detecting the concentration of oxygen in exhaust gases (emissions produced as a result of combustion of a fuel) emitted from internal combustion engines for motor vehicles. Such a known oxygen sensor utilizes an oxygen-ion conductive solid electrolyte such as zirconia ceramics, and is operated according to the principle of an oxygen concentration cell In recent motor vehicles, the internal combustion engine is usually controlled so that an air/fuel ratio of an air-fuel mixture to be supplied to the engine is maintained at a desired value For this purpose, the oxygen sensor as indicated above is employed to detect the oxygen concentration of the exhaust emission, which has a given relationship with the air/fuel ratio of the air-fuel mixture. With the oxygen concentration of the exhaust emission detected, the fuel supply to the engine is controlled in a feedback fashion.

The known oxygen sensor or oxygen concentration detecting device of the type described above incorporates an oxygen sensing element wherein two electrodes are disposed on a substrate or body of an oxygen-ion conductive solid electrolyte. One of the two electrodes serves as a measuring electrode which communicates with a fluid to be measured (measurement fluid) such as exhaust gases, while the other electrode serves as a suitable reference electrode which communicates with a reference gas such as an ambient air. In operation, the oxygen sensing element produces an electromotive force, based on a difference in the oxygen concentration between the atmospheres communicating with the measuring and reference electrodes, according to the principle of an oxygen concentration cell. Conventionally, the two electrodes are formed principally of platinum, by plating, sputtering, or other techniques.

However, the known oxygen sensing element using the platinum electrodes as indicated above are not capable of accurately detecting or determining the air/fuel ratio of the air-fuel mixture supplied to the engine, based on the oxygen concentration of the exhaust gases or emissions produced by the engine. Described more specifically, the measuring electrode is not able to sufficiently reduce unburned components, in particular, NOx, contained in the exhaust gases, and is therefore incapable of detecting the compound oxygen in the unburned components. That is, the oxygen sensing element measures the oxygen concentration, without taking the NOx into account. As a result, it is very difficult to control the air/fuel ratio so as to reduce the NOx, based on the detected oxygen concentration, in the known oxygen sensing element.

Various structures of the electrodes have been proposed to improve the durability of the electrodes. For example, laid-open Publication No. 60-144659 (published on July 31, 1985) of Japanese Patent Application No. 59-000039 proposes a technique for maintaining the reliability of a detecting element (oxygen sensing element) for a prolonged period of time, by applying rhodium salt/water or organic solvent to a platinum electrode plated on a solid electrolyte body, and thereby reducing an internal impedance of the element. Further, laid-open Publication No. 61-17950 (published on Jan. 25, 1986) of Japanese Patent Application No. 59-138597 proposes a technique for increasing the life expectancy of a sensing element, by baking a paste of a noble metal applied to the surface of a solid electrolyte body, and forming a metal layer active as a catalyst on the baked noble metal layer, thereby improving an adhering force between the sintered solid electrolyte body and electrode. Another technique for assuring an improved life expectancy of a sensing element is proposed in laid-open Publication No. 61-30760 (published on Feb. 13, 1986) of Japanese Patent Application No. 59-153775, wherein a measuring electrode is covered by a layer of rhodium or palladium or layers of both, to avoid contamination of the electrode by lead contained in the exhaust emissions to be measured.

However, the provision of rhodium or palladium, or catalytic activation species or points on the electrode (platinum electrode) is intended merely for improving the durability of the sensor, but is not improving the detecting characteristic of the sensor, to enhance the property of exhaust emissions produced by motor vehicles, which are controlled based on the output of the sensor.

Thus, the proposed techniques described above do not depart from a technique for pursuing an improvement in the durability of the sensor. More particularly, the techniques disclosed in laid-open Publications Nos. 60-144659 and 61-30760 are nothing but a technique wherein an electrode material applied by plating, deposition, sputtering or other methods is provided with a catalytically active material (rhodium, palladium, etc.). The proposed electrode layer has a small thickness and a small surface area of contact with the solid electrolyte body, and cannot be expected to provide a sufficiently high effect of reducing unburned components contained in the exhaust emissions. Therefore, the sensor utilizing the proposed electrode structure is not able to accurately detect the air/fuel ratio of the air-fuel mixture which produces the exhaust emissions containing NOx. In the technique disclosed in the laid-open Publication No. 61-17950, the metal layer as a catalytic activation layer is formed by applying an aqueous solution of rhodium chloride/palladium chloride to a solid electrolyte body and firing the applied unfired catalytically active material. Accordingly, the thickness of the fired electrode layer is small, and the thickness of the catalytic activation layer is also limited. Hence, the electrode obtained by this technique does not have a sufficiently high effect in reducing the unburned components of the exhaust emissions, and cannot be considered to contribute to an improvement in the detecting accuracy of the sensor, i.e., an improvement in the accuracy of determination of the air/fuel ratio of the air-fuel mixture.

Also, U.S. Pat. No. 4,199,425 discloses a technique wherein a porous ceramic overcoat which covers an electrode is provided with rhodium which serves as a reducing catalyst for promoting chemical equilibrium of oxidizable exhaust gas components on the electrode. Since the catalyst is applied to the overcoat by impregnation or chemical deposition, the amount of the catalyst applied to the overcoat is extremely limited. Further, since the catalyst is given to the overcoat, there exists only a comparatively small number of reaction points among the catalyst, platinum and solid electrolyte (zirconia). Therefore, the electrode covered by the overcoat cannot be considered to have sufficiently high ability to reduce the unburned components of the exhaust emissions, and the sensor using the electrode does not permit accurate detection of the air/fuel ratio of the air-fuel mixture which produces the exhaust emissions containing NOx.

SUMMARY OF THE INVENTION

It is therefore a principal object of the present invention to provide an electrode structure of an oxygen sensor which has excellent ability of purifying exhaust gases as a fluid to be measured, and which is capable of accurately determining the air/fuel ratio of an air-fuel mixture, by detecting the oxygen concentration of the exhaust gases produced as a result of combustion of the air-fuel mixture, even where the exhaust gases contain unburned components such as NOx.

The above object may be attained according to the principle of the present invention, which provides an electrode structure formed on an oxygen-ion conductive solid electrolyte body of an oxygen sensing element such that the electrode structure communicates with a measurement fluid to be measured, for detecting the concentration of oxygen in the fluid, wherein the electrode structure is formed of a porous cermet layer having a thickness of at least 3 microns. The porous cermet layer includes as major components thereof an oxygen-ion conductive solid electrolyte, and at least two platinum-group metals which are selected from the platinum group and which includes platinum and rhodium. A content of rhodium and a total content of the platinum-group metal or metals are determined so as to satisfy the following formulas:

$R/M = 0.2$ to $0.8$ $M/(SE+M) = 0.3$ to $0.8$ where,

R: volume % of rhodium included in the porous cermet layer, as a part of the at least two platinum-group metals, M: total volume % of the at least two platinum-group metals included in the porous cermet layer, SE: volume % of the oxygen-ion conductive solid electrolyte included in the porous cermet layer.

The electrode structure according to the present invention, which serves as a measuring electrode exposed to the measurement fluid, is formed of the cermet which is a mixture of the at least two platinum-group metal components and the ceramic component. Accordingly, the thickness of the electrode structure can be increased. Further, the instant electrode structure has an increased number of contact points or reaction points between the platinum-group metal components, and the ceramic component in the form of an oxygen-ion conductive zirconia or other solid electrolyte material. Consequently, the electrode structure is capable of promoting chemical equilibrium of unburned constituents in the measurement fluid such as carbon monoxide (CO), hydrocarbons (HC) and nitrogen oxides (NOx) on or adjacent to the structure, whereby the air/fuel ratio of an air-fuel mixture can be precisely determined by detecting the oxygen concentration of exhaust emissions as the measurement fluid, which are produced from the air-fuel mixture. That is, the instant electrode structure is highly adapted to control combustion of the air-fuel mixture so as to purify the exhaust gases by means of a three-way catalyst, or minimize the toxic exhaust emissions (CO, HC, NOx) which are emitted through the three-way catalyst.

In the electrode structure according to the present invention, the three components of the electrode composition, namely, rhodium, platinum (and other platinum-group metal or metals selected as needed) and solid electrolyte, are present in suitably selected proportions or ratios, such that the three components (at least three components) provide a plurality of reaction points in the direction of thickness of the structure. Consequently, the electrode structure enables the sensor to accurately detect the $\lambda$ point of an air-fuel mixture, even where the exhaust gas components or volume ratios thereof greatly vary depending upon the burning condition of the air-fuel mixture, as in the internal combustion engines for automotive vehicles wherein the combustion conditions considerably fluctuates under varying running conditions of the vehicle. Based on the detected $\lambda$ point, the air-fuel ratio of the air-fuel mixture supplied to the engine, or the combustion condition of the engine, can be controlled so that NOx, CO and other unburned components of the exhaust gases can be reduced.

Moreover, the durability of the instant electrode structure serving as the measuring electrode exposed to the measurement fluid is effectively improved, since the structure is formed of a cermet with a sufficient thickness according to the present invention.

BRIEF DESCRIPTION OF THE DRAWINGS

The above and optional objects, features and advantages of the present invention will be better understood by reading the following detailed description of the invention, when considered in connection with the accompanying drawings, in which.

DETAILED DESCRIPTION OF THE INVENTION

Figure 1:
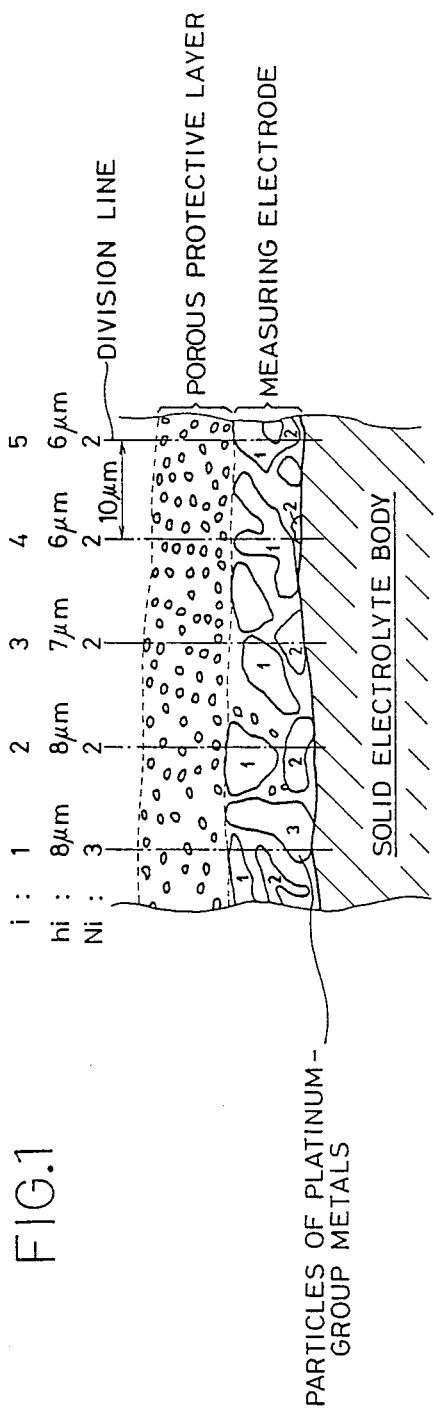
FIG. 1 is an illustrative cross sectional view of one embodiment of an electrode structure of the present invention, indicating a manner of obtaining an average particle size of platinum-group metals.

As described above, the measuring electrode according to the invention, which is disposed on the solid electrolyte body of the oxygen sensing element such that the electrode structure is exposed to the measurement fluid, is formed of the porous cermet whose major components consist of an oxygen-ion conductive solid electrolyte such as zirconia similar to that used for the solid electrolyte body of the element, and at least two platinum-group metal components which include rhodium and platinum. The content of rhodium and the total content of the platinum-group metal components of the cermet layer should satisfy the following equations:

$$R/M = 0.2 \text{ to } 0.8$$

$$M/(SE+M) = 0.3 \text{ to } 0.8$$

where,

R: volume % of rhodium included in the porous cermet layer, as one of the platinum-group metals, M: total volume % of the platinum-group metals included in the porous cermet layer, SE: volume % of the oxygen-ion conductive solid electrolyte included in the porous cermet layer.

In the cermet electrode structure of the above-indicated composition, reaction points between the platinum-group metals and the solid electrolyte are formed in an effective manner with respect to the measurement fluid. Where the electrode structure has a thickness of at least 3 microns, preferably about 5-20 microns, a plurality of reaction points are provided in the direction of thickness of the electrode. This comparatively large number of reaction points within the electrode structure enables the sensing element to detect the measurement fluid with improved precision, and accurately determine the air/fuel ratio of the air-fuel mixture.

Generally, the exhaust emissions from an automotive engine have a tendency wherein the amount of CO decreases with an increase in the amount of NOx, while conversely the CO amount increases with a decrease in the NOx amount. In the cermet electrode according to the invention, the ratio by volume of M/(SE+M) is held within a range of 0.3-0.8, in which the air/fuel ratio of the air-fuel mixture can be accurately determined by detecting the exhaust emissions. Thus, the air/fuel ratio can be suitably controlled, and at the same time the NOx and CO constituents can be effectively minimized. Outside the above-indicated range of the M/(SE+M) ratio, a sufficient reduction in the amounts of NOx and CO cannot be expected.

If the M/(SE+M) ratio is lower than 0.3, the total content of the metal components (electrically conductive components) of the electrode is excessively low, and the internal resistance of the sensing element unfavorably increases, thereby adversely affecting the sensing characteristics of the sensor. In the worst case, the electrode suffers from electrical discontinuity. In the case where the nominal M/(SE+M) ratio is set in the neighborhood of 0.3, the ratio of the actually produced electrode structure may more or less fluctuate due to the varying factors associated with the manufacture, and therefore there is some possibility of deterioration of the sensing characteristics due to the electrical discontinuity of the electrode. In light of this tendency, it is desirable that the nominal ratio of M/(SE+M) be set 0.4 or higher. If the M/(SE+M) ratio exceeds 0.8, on the other hand, the total metal content of the electrode composition becomes so high as to reduce the number of the electrode reaction points, i.e., points formed by three components of platinum, rhodium (and other platinum metal or metals, if any) and solid electrolyte at which the electrode reaction occurs with a fluid to be measured. In this case, too, the electrode structure cannot assure an improvement in the property of the exhaust emissions detected by the sensor.

As indicated above, the platinum-group metals of the cermet electrode according to the invention should include rhodium as well as platinum, as catalytic activation species. These two platinum-group metal components cooperate with the solid electrolyte to form the above-indicated reaction or contact points which are effective to reduce the NOx amount of the exhaust emissions. It will be obvious that the platinum-group metals may include other elements of the platinum group, such as palladium, iridium, ruthenium and osmium. Further, the ratio R/M of rhodium to the total content of the platinum-group metals is held within a range of 0.2-0.8. This rhodium ratio also contributes to accurate determination of the air/fuel ratio, even where the exhaust emissions contain unburned components such as NOx. Namely, the output of the sensor using the instant electrode structure can be used to control the air/fuel ratio of the air-fuel mixture and the combustion condition of the mixture, so that CO as well as NOx of the exhaust emissions can be effectively reduced.

If the R/M ratio is lower than 0.2 or higher than 0.8, the number of the reaction points formed by the three components, i.e., platinum, rhodium (and other platinum-group metal or metals, if any) and solid electrolyte, is too small to permit accurate detection of the measurement fluid and improve the emission property, whereby the amount of NOx included in the exhaust emissions undesirably increases. In particular, where the rhodium content exceeds the upper limit, the operating characteristics of the electrode and the property of the exhaust emissions (controlled responsive to the sensor) may be deteriorated due to oxidation of rhodium during use of the sensor. In this sense, it is preferable that the R/M ratio be 0.7 or lower.

In the cermet electrode structure of the invention, it is preferable that rhodium is distributed such that the rhodium content is higher in an outer thickness portion of the cermet layer adjacent to the measurement fluid, than in an inner thickness portion which contacts the surface of the solid electrolyte body of the oxygen sensing element. In this case, the sensing element is highly responsive to the measurement fluid, and provides enhanced measuring accuracy. For example, such rhodium distribution may be attained by fabricating the cermet electrode structure of a plurality of cermet layers, such that the rhodium content increases in a direction from the innermost layer contacting the solid electrolyte body, toward the outermost layer exposed to the measurement fluid. Where the cermet electrode structure consists of a laminar structure consisting of two cermet layers, each layer has a thickness of about 1.5-10 microns.

The cermet electrode structure according to the invention is generally formed by first preparing a cermet paste which contains at least two platinum-group metals (which may be in the form of alloys) including platinum and rhodium, and an oxygen-ion conductive solid electrolyte material, and then applying by printing the prepared paste to the surface of a fired or calcined solid electrolyte body, or a green sheet of the solid electrolyte body. The porous cermet electrode structure is obtained by firing the applied cermet layer on the solid electrolyte body. When the cermet paste is prepared, it is necessary to consider various factors such as particle sizes of the appropriate powdered materials (metal particles and solid electrolyte particles), an amount and a kind of a binder, a manner of mixing the materials, and inclusion of additives such as powdered carbon which is easily scattered during baking or firing and allows for formation of pores within the obtained electrode structure. In any case, the above factors must be considered so that the fired cermet structure is given a suitable porosity and has suitable particle sizes of the platinum-group metals or alloys thereof.

To avoid oxidation of the materials of the cermet structure during baking or firing, it is advantageous that the average particle size of the platinum-group metals, particularly, rhodium powder or rhodium alloy powder, be at least 0.05 micron.

As discussed above, the microstructure of the cermet electrode of the invention should have a comparatively large number of gas reaction portions or points, in order to be sufficiently responsive to the exhaust gases containing NOx and other unburned components, for accurate determination of the air/fuel ratio of the air-fuel mixture, which is controlled by detecting the exhaust gases. For this end, it is desirable that the average particle size of the platinum-group metals or their alloys be not greater than two-thirds ($\frac{2}{3}$), preferably, not greater than one-third ($\frac{1}{3}$), of the thickness of the electrode layer itself. Where the exhaust gases contain a relatively large amount of oxidizable components, for instance, where the exhaust gases are oxygen-rich gases produced as a result of combustion of an air-rich air-fuel mixture supplied to an automotive engine, it is desirable that the average particle size of the platinum-group metals or their alloys, particularly the average particle size of rhodium or its alloy, of the cermet electrode be at least 0.1 micron, in order to avoid the oxidation of the platinum-group materials.

Usually, the platinum-group metal particles or grains within the fired electrode structure have irregular shapes. For instance, the metal particles of the sintered electrode structure have relatively thin flat configurations, or sharp prongs projecting from the surface of the particles. In view of this, the term "average particle size of the platinum-group metals" of the electrode structure used herein should be interpreted to mean an average particle size which is calculated as described below.

Initially, the electrode structure is cut in a plane perpendicular to the surface of the sensing element, and a plurality of parallel division lines (e.g., five division lines) are provided on the cut surface of the electrode structure, at a suitable interval of about 10 microns, as indicated in FIG. 1. Then, the number "Ni" of the platinum-group metal particles which intersect each division line is counted, and the thickness "hi" of the electrode structure as measured along each division line is measured. The average particle size of the platinum-group metals is then calculated according to the following formula:

$$0.1 \ \mu m \leq \frac{h1 + h2 + \ldots + hi}{N1 + N2 + \ldots + Ni} \leq 2H/3 \ (preferably, H/3)$$

$$H = (h1 + h2 + \ldots + hi)/i$$

where,
i: number of the division lines,
H: average thickness of the electrode structure In the specific example shown in FIG. 1, the average thickness "H" of the electrode structure, and the average particle size of the platinum-group metals are calculated as follows:

$$H = (8 + 8 + 7 + 6 + 6)/5 = 7 \ \mu m$$

$$\frac{h1 + \ldots + h5}{N1 + \ldots + N5} = \frac{8 + 8 + 7 + 6 + 6}{3 + 2 + 2 + 2 + 2} = 3.2 \ \mu m$$

Therefore, $$0.1 \ \mu m \leq \frac{h1 + \ldots + h5}{N1 + \ldots + N5} = 3.2 \leq 2H/3 = 4.7 \ \mu m$$

For improved durability of the electrode structure and accordingly improved durability of the sensor, it is desirable that the cermet electrode layer be covered by a porous protective layer which has a thickness of about 10–400 microns, preferably about 50–200 microns. This protective layer may be formed by suitable techniques such as plasma coating, printing, or deposition, and is usually formed of a ceramic material. In one advantageous method for forming the protective layer, a selected ceramic powder is intimately mixed with a binder or other suitable solvent, and the obtained mixture is applied in the form of a tape, as by a doctor-blade technique, such that the applied tape covers the unfired electrode structure, and if necessary, a portion of the solid electrolyte body near the electrode structure, as needed. The thus formed unfired protective layer is co-fired with the unfired electrode structure. The fired protective layer is given a porous structure.

Where the porous protective tape is formed as described above, the porosity of the layer is easily adjustable so as to effectively minimize a variation in the operating characteristics of the sensing element. Further, the ceramic material of the protective tape reacts with the ceramic material (solid electrolyte) contained in the electrode structure, during sintering of these ceramic materials, whereby the porous protective layer is formed as an overcoat for the cermet electrode layer, with an extremely large adhering force therebetween. In this respect, the sensor durability is further improved.

The material for the porous protective layer may be selected from known ceramic materials such as spinel or alumina. However, the protective layer is preferably formed of a ceramic material whose major component (more than 50% of which) consists of zirconia or other solid electrolyte. When the electrode structure is covered by a porous protective layer whose major component consists of a solid electrolyte, the electrode structure may have an increased number of reaction points at which the platinum-group metals, solid electrolyte and measurement fluid coexist with each other. Further, the sensor does not suffer from cracks due to a difference in the thermal expansion coefficient between the porous protective layer and the underlying solid electrolyte substrate.

Figure 2:
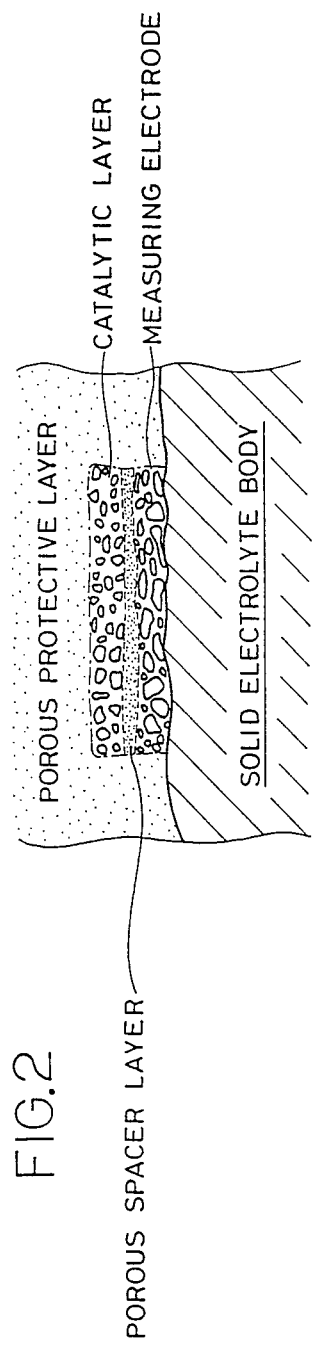
FIG. 2 is an illustrative cross sectional view of another embodiment of the electrode structure of the invention, showing a porous spacer layer, a catalytic layer and a porous protective layer, which are successively formed on the electrode layer.

In another embodiment of the invention as illustrated in FIG. 2, the cermet electrode layer is provided with a porous spacer layer formed thereon, and a porous catalytic layer formed on the spacer layer. The porous spacer layer may be formed in the same manner as the porous protective layer. The porous catalytic layer functions as a catalyst for reducing oxides of nitrogen (NOx), and has a thickness preferably within a range of about 4–20 microns. Where the thickness of the catalytic layer falls within the above preferred range, the porous spacer layer should have a thickness of about 1–30 microns, preferably, 1–10 microns. It will be understood that a porous protective layer may be formed so as to cover the laminar structure which consists of the cermet electrode layer, porous spacer layer and catalytic layer, as indicated in FIG. 2. In any case where the catalytic layer is provided, the catalyst of the catalytic layer first reacts with the oxidizable or unburned components of a measurement fluid such as exhaust gases, thereby reducing the total amount of these unburned components before the exhaust gases reach the cermet electrode layer. Accordingly, the electrode structure provided with such a catalytic layer enables the sensor to accurately detect exhaust gases and thereby precisely determine the air/fuel ratio of an air-fuel mixture that produces the exhaust gases, even where the exhaust gases contain a large amount of oxidizable or unburned components. For the above reason, the rate of flow of the measurement fluid to the electrode layer may be comparatively higher if the catalytic layer is provided. Therefore, a porous overcoat such as the porous protective layer formed to restrict the flow of the fluid (gaseous fluid) to the electrode layer may have a comparatively reduced thickness and an increased porosity. This means an increased rate of permeation of the fluid through the porous overcoat, and an accordingly shorter response of the oxygen sensing element.

Preferably, a major component of the catalytic layer consists of rhodium. To improve adhesion of the catalytic layer to the porous spacer layer and the porous protective layer, it is desirable that a suitable ceramic material such as $ZrO_2$, $Al_2O_3$ or $TiO_2$ be included in the catalytic layer, so that the major rhodium component and the ceramic material form a cermet structure. The porous spacer layer acts to protect the catalytic layer from contacting and reacting with the components of the electrode composition, and from thereby losing its catalytic function during manufacture and use of the sensor Thus, the spacer layer is effective to assure excellent initial performance and high durability of the oxygen sensor. However, it is preferred that the thickness of the spacer layer be as small as possible.

The solid electrolyte body on which the cermet electrode structure according to the invention is formed may be formed of a known oxygen-ion conductive solid electrolyte such as zirconia ceramics, $SrCeO_3$, or a solid solution of $Bi_2O_3$ and rare earth oxides. The solid electrolyte body may take a suitable configuration as known in the art, such as a rod, a plate or a tubular body closed at its one end. The principle of the present invention is applicable to a measuring electrode formed on such a solid electrolyte body of an oxygen sensing element.

EXAMPLES

To further clarify the concept of the present invention, some specific examples embodying the invention will be described with a certain degree of particularity. However, it is to be understood that the invention is not limited to the details of the illustrated example, but the invention may be embodied with various changes, modifications and improvements, which may occur to those skilled in the art, without departing from the spirit of the invention.

In the following description of the examples, ratios or percentages are based on volumes, unless otherwise specified.

EXAMPLE 1

A planar solid electrolyte body (substrate of a sensing element) was formed of a zirconia solid electrolyte material prepared by a solid solution containing 6 mole % of $Y_2O_3$, such that an air passage communicating with the ambient air is formed through the formed solid electrolyte body. On an inner surface of the solid electrolyte body which partially defines the air passage, there was formed a reference electrode which communicates with the air introduced in the air passage. The reference electrode was formed by printing of an electrically conductive material whose major component consists of platinum. On a portion of an outer surface of the solid electrolyte body which is opposite to the reference electrode, there was formed a two-layered measuring electrode. Described more specifically, the measuring electrode consisted of a first layer and a second layer which were formed by printing of a first and a second electrode paste, respectively. The first electrode paste consisted of a powder of an electrically conductive material whose major component is platinum, and a powder of the same zirconia solid electrolyte material as used for the solid electrolyte body. The second electrode paste is a cermet consisting of 60% of a rhodium powder, and 40% of the same zirconia solid electrolyte powder as used for the first electrode paste. The planar solid electrolyte body with the reference and measuring electrodes thus formed thereon was then dried, and fired at 1400° C. Successively, a ceramic material whose major component consisted of spinel was applied by a plasma-spraying method to the surface of the two-layered measuring electrode, whereby a porous protective layer having a thickness of about 50 microns was formed. The solid electrolyte body with the elecrodes and protective layer was then maintained for two hours at 400° C., for hydrogen reducing treatment. In this manner, the intended oxygen sensing element was prepared.

The prepared oxygen sensing element was cut in order to observe a cut surface of the measuring electrode by a scanning electron microscope. The cut surface of the measuring electrode was further analyzed by an energy dispersional X-ray microanalyzer. The observation and analysis revealed that platinum was present in a greater amount in an inner thickness portion (first electrode layer) of the measuring electrode which is adjacent to the solid electrolyte body, while rhodium was present in a greater amount in an outer thickness portion (second thickness portion) of the measuring electrode which is adjacent to the ambient atmosphere (measurement fluid). It was found that the gradients of concentration of platinum and rhodium are formed through the whole thickness of the two-layered measuring electrode consisting of the first and second layers.

Figure 3:
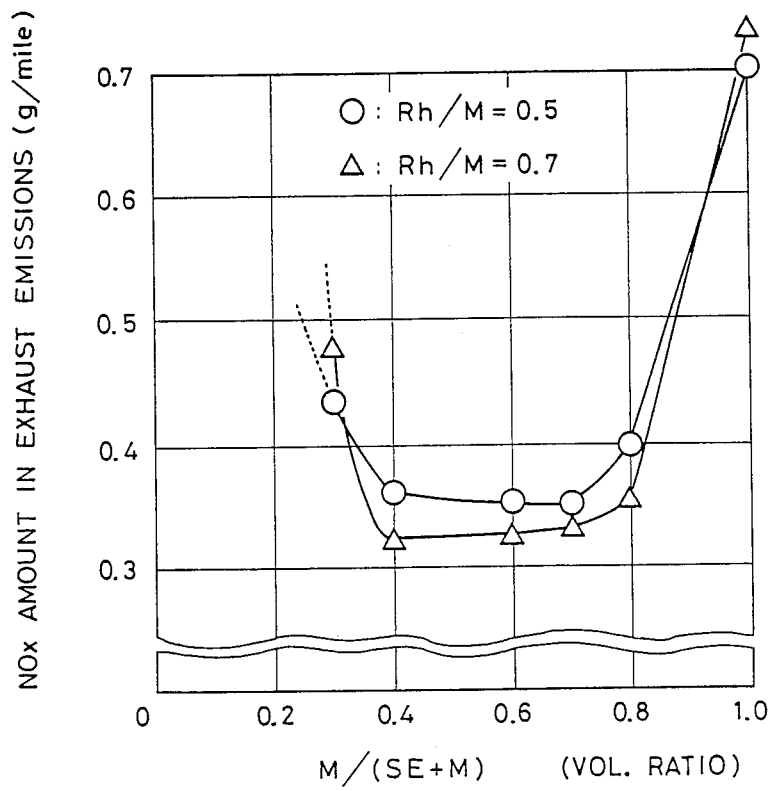
FIGS. 3 through 5 are graphs illustrating relationships between various compositions of electrode structures of Example 1, and an emission property (NOx amount) of exhaust gases detected by the sensors using the electrode structures.
Figure 4:
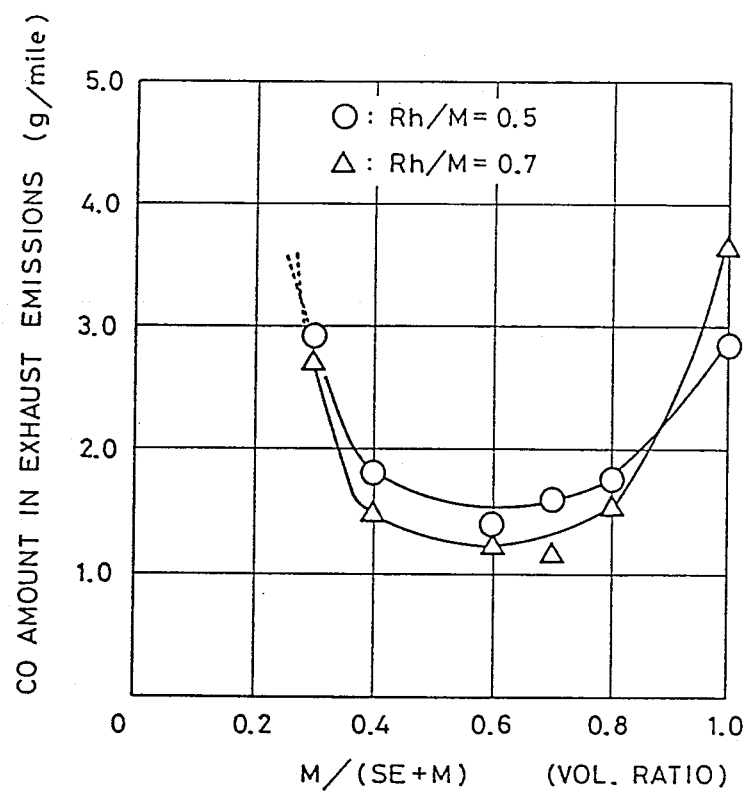
Figure 5:
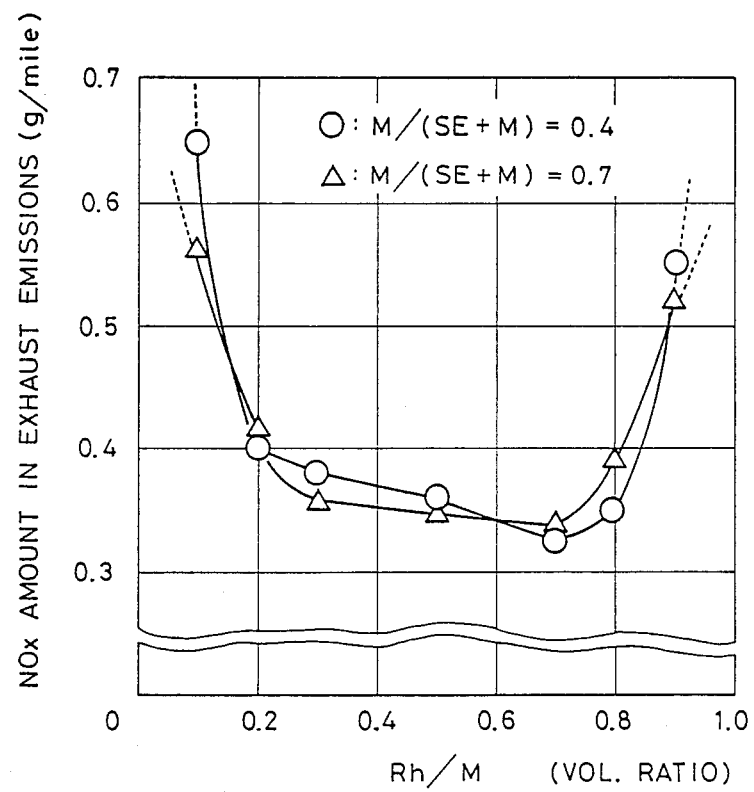

Various oxygen sensing elements were prepared with respective two-layered measuring electrodes as described above, which have different compositions of the first and second electrode layers, so that the compositions of the measuring electrodes as a whole have different ratios of M/(SE+M), as indicated in FIGS. 3 and 4, and different ratios of Rh/M, as indicated in FIG. 5. The reference character "M" represents a total volume % of rhodium particle and platinum particle in the measuring electrodes, and the reference character "Rh" represents a volume % of rhodium particle in the electrodes, while the reference character "SE" represents a volume % of the solid electrolyte material in the electrodes. The specimens of FIGS. 3 and 4 having different M/(SE+M) ratios have the Rh/M ratio of 0.5 or 0.7, while the specimens of FIG. 5 having different Rh/M ratios have the M/(SE+M) ratio of 0.4 or 0.7.

The prepared oxygen sensing elements were tested for their operating characteristics, according to the LA-4 Emission Control Method, in exhaust gases which were produced by a 4-cylinder, 2000cc-displacement engine with a fuel injector and a three-way catalyst. The sensing elements were evaluated by analyzing the NOx and CO amounts of the exhaust emissions, which were emitted during the testing operations. The results of the test are shown in FIGS. 3-5.

It follows from FIGS. 3 and 4 that the property of the exhaust emissions, i.e., the amounts of NOx and CO of the exhaust emissions considerably varied depending upon the compositions of the two-layered measuring electrodes as a whole. Namely, it was recognized that the amounts of both NOx and CO emissions were sufficiently small where the volume ratio of M/(SE +M) was held within a range of 0.3–0.8. Regarding the specimens of FIG. 5, it was confirmed that the amounts of both NOx and CO were sufficiently small where the volume ratio of Rh/M was held within a range of 0.2–0.8. These results of the test indicate that the cermet structure of the measuring electrode according to the principle of the present invention should have the M/(SE+M) ratio within the range of 0.3–0.8, and the Rh/M ratio within the range of 0.2–0.8, so that the air/fuel ratio of an air-fuel mixture supplied to an engine can be accurately determined, by detecting the oxygen concentration of exhaust gases produced as a result of combustion of the air-fuel mixture, and so that the combustion of the air-fuel mixture in the engine can be controlled in an optimum manner, based on the output of the oxygen sensing element.

EXAMPLE 2

As in Example 1, a cermet measuring electrode was formed by printing on a zirconia solid electrolyte body with a reference electrode, by using a paste which consisted of a powder mixture of rhodium, platinum and zirconia. The solid electrolyte body with the cermet measuring electrode and the reference electrode was dried, and fired in air at a temperature of 1400° C. A porous protective layer having a thickness of 50 micron was then formed by spraying spinel over the cermet measuring electrode. In the above manner, three oxygen sensing elements were prepared, with the cermet measuring electrodes having different compositions. That is, the measuring electrodes of the three sensing elements have the same M/(SE+M) ratio of 0.6, but have respective different Rh/M ratios of 0.3, 0.5 and 0.7. These three specimens exhibited results almost similar to the specimens of Example 1 having the same cermet electrode compositions (Rh-Pt-ZrO$_2$), although the NOx amount of the exhaust emissions was increased by about 0.05g/mile. It was confirmed that the instant specimens showed sufficiently superior results, to that of a sensing element whose measuring electrode does not contain rhodium.

EXAMPLE 3

A zirconia porous spacer layer having a thickness of 5 microns was formed by printing on the cermet measuring electrode of each specimen of Example 1. On this porous spacer layer, there was formed by printing a porous catalytic layer having a thickness of about 10 microns, which consisted of rhodium and zirconia, or rhodium, platinum and zirconia. After the specimens were dried and fired at 1400° C., a porous protective layer having a thickness of about 50 microns was formed by spraying spinel over the catalytic layer of each specimen. Thus, the various oxygen sensing elements corresponding to those of Example 1 were prepared, with the porous spacer, catalytic and protective layers.

These specimens with the Rh-ZrO$_2$ or Rh-Pt-ZrO$_2$ catalytic layer formed on the cermet electrode via the spacer layer demonstrated better results relating to the reduction of the NOx and CO emissions, than a sensing element which does not have such a catalytic layer. Further, a durability test of the specimens on a simulation engine bench was conducted. The durability was evaluated by measuring the operating time length until the electromotive force induced by the sensing element declines to a ⅔ level of the initial value. The test showed a durability increase of about 50% of the instant specimens, over a known sensing element with a conventionally plated measuring electrode. The test also showed a durability increase of about 20% of the instant specimens, over a sensing element of the present invention which did not have a catalytic layer on the cermet electrode.

EXAMPLE 4

Various oxygen sensing elements were prepared, by modifying the compositions of the first and second electrode layers used in Example 1. Namely, 10% or 20% of the platinum content of the first electrode layer of Example 1 was replaced by palladium in Example 4. However, the volume ratio of (Pt+Pd)/(SE+Pt+Pd) was maintained at 0.6. Thus, the first electrode layer was formed with a thickness of about 7 microns. On this first electrode layer, there was formed a second electrode layer having a thickness of about 7 microns, which consists of rhodium and zirconia such that the ratio of Rh/(ZrO$_2$+Rh) is 0.6. Thus, the two-layered porous cermet electrodes (measuring electrodes) were formed on the respective sensing elements, but with different M/(SE+M) ratios as described below.

Figure 6:
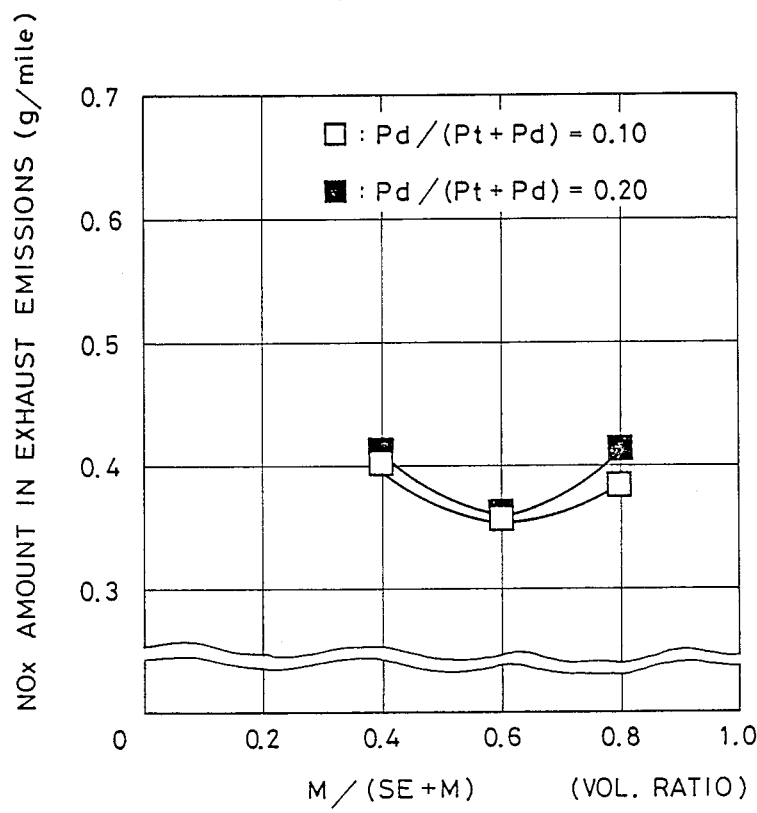
FIG. 6 is a graph illustrating relationships similar to those of FIGS. 3-5, which were obtained in Example 6.

That is, the cermet measuring electrodes of three groups of the specimens have the M/(SE+M) ratios of 0.4, 0.6 and 0.8 (M=Pt+Rh+Pd, Rh/M=0.5), respectively, as indicated in FIG. 6. The operating characteristics of the specimens were evaluated in the same manner as in Example 1. The graph of FIG. 6 shows relationships between the NOx amount of the exhaust emissions and the M/(SE+M) ratio of the cermet electrodes of the present Example 4, which are almost the same as obtained in Example 2 wherein the cermet electrodes consisted principally of Pt.

Modified sensing elements were prepared by adding about 5 parts by volume of Ni, Fe, Cu or other transition elements, or oxides thereof, or Au, to 100 parts by volume of the cermet electrode compositions of Example 4. This additive was included in one of the first and second layers of the two-layered measuring electrode. A test revealed virtually no influence of the additive on the operating characteristics of the sensing elements (on the property of the exhaust emissions).

EXAMPLE 5

Oxygen sensing elements each having a two-layered measuring electrode were prepared in the same manner as in Example 1, and tested on the engine as used in Example 1, in order to check a relationship between the thickness of the measuring electrodes and the NOx amount.

The test revealed a sufficient decrease in the NOx amount, where the measuring electrodes have a thickness of at least 3 microns, as indicated in Table 1 below. The test also showed a deteriorated operating response of the sensing elements, where the electrode thickness exceeds 20 microns.

TABLE 1

|  | Measuring Electrodes | | Thickness ($\mu$m) | NOx (g/mile) |
| --- | --- | --- | --- | --- |
|  | R/M | M/(SE + M) | | |
| Comparative | 0.5 | 0.6 | 0.5–2.5 | 0.55 |
| Invention (1) | " | " | 3–4.5 | 0.41 |
| (2) | " | " | 5–8 | 0.35 |
| (3) | " | " | 13–17 | 0.35 |
| (4) | " | " | 15–25 | 0.33 |

An investigation on the produced sensing elements (fired sensing elements) showed that the ratios R/M and M/(SE+M) were held within a range of 10% of the values indicated in Table 1.

The thicknesses of the measuring electrodes as indicated in Table 1 are a maximum and a minimum value as measured on a cut surface of each electrode as illustrated in FIG. 1.

The NOx amount indicated in the table is an average value obtained on three pieces of each specimen.

What is claimed is:

1. An electrode structure formed on an oxygen-ion conductive solid electrolyte body of an oxygen sensing element, such that the electrode structure communicates with a measurement fluid to be measured, for detecting a concentration of oxygen in said fluid, comprising:

a porous cermet layer having a thickness of at least 3 microns, said porous cermet layer including as major components thereof an oxygen-ion conductive solid electrolyte, and at least two platinum-group metals which are selected from the platinum group and which include platinum and rhodium, a content of said rhodium and a total content of said at least two platinum-group metals being determined so as to satisfy the following formulas:

R/M=0.2 to 0.8

M/(SE+M)=0.3 to 0.8 where,
R: volume % of said rhodium included in said porous cermet layer, as a part of said at least two platinum-group metals,
M: total volume % of said at least two platinum-group metals included in said porous cermet layer,
SE: volume % of said oxygen-ion conductive solid electrolyte included in said porous cermet layer.

2. An electrode structure according to claim 1, wherein said porous cermet layer includes a higher content of said rhodium in a direction of thickness of said layer at a portion adjacent to said measurement fluid, than in a direction of thickness of said layer at a portion which contacts said oxygen-ion conductive solid electrolyte body.

3. An electrode structure according to claim 1, wherein said porous cermet layer is a laminar structure consisting of a plurality of layers, the content of said rhodium in said plurality of layers increasing in a direction of thickness of said laminar structure, from an innermost one of said plurality of layers which contacts said solid electrolyte body toward an outermost one of said plurality of layers adjacent said measurement fluid.

4. An electrode structure according to claim 1, wherein said porous cermet layer is covered by a porous protective layer formed thereon.

5. An electrode structure according to claim 4, wherein said porous protective layer is formed of a ceramic material.

6. An electrode structure according to claim 1, wherein said cermet layer is formed from an unfired material including a powder of rhodium or rhodium alloy which has an average particle size of at least 0.05 micron.

7. An electrode structure according to claim 1, wherein said at least two platinum-group metals of said cermet layer consist of a powder having an average particle size not greater than two-thirds of the thickness of said cermet layer.

8. An electrode structure formed on an oxygen-ion conductive solid electrolyte body of an oxygen sensing element such that the electrode structure communicates with a measurement fluid to be measured, for detecting a concentration of oxygen in said fluid, comprising:

a porous cermet layer having a thickness of at least 3 microns, said porous cermet layer including as major components thereof an oxygen-ion conductive solid electrolyte, and at least two platinum-group metals which are selected from the platinum group and which include platinum and rhodium, a content of said rhodium and a total content of said at least two platinum-group metals being determined so as to satisfy the following formulas:

R/M=0.2 to 0.8

M/(SE+M)=0.3 to 0.8 wherein,
R=volume % of said rhodium included in said porous cermet layer, as part of said at least two platinum-group metals,
M=total volume % of said at least two platinum-group metals included in said porous cermet layer,
SE=volume % of said oxygen-ion conductive solid electrolyte included in said porous cermet layer;
wherein said porous cermet layer is covered by a porous spacer layer, and a porous catalytic layer formed on said porous spacer layer, said catalytic layer being capable of reducing oxides of nitrogen.

9. An electrode structure according to claim 8, wherein said porous catalytic layer includes rhodium as a major component thereof.

10. An electrode structure according to claim 8, wherein said porous spacer layer consists of a ceramic layer.

* * * * *